United States Patent [19]
Pagani et al.

[11] 4,100,273
[45] Jul. 11, 1978

[54] **ANTIBIOTIC SUBSTANCE FROM *ACTINOPLANES SARVEPARENSIS* CBS 305.76 (ANTIBIOTIC L 13365)**

[75] Inventors: Hermes Pagani; Francesco Parenti; Carolina Coronelli; Giorgio Tamoni, all of Milan, Italy

[73] Assignee: The Dow Chemical Company, Milan, Italy

[21] Appl. No.: 802,215

[22] Filed: May 31, 1977

[30] Foreign Application Priority Data
Jun. 29, 1976 [GB] United Kingdom ............... 26934/76

[51] Int. Cl.² ............................................ A61K 35/74
[52] U.S. Cl. .................................. 424/117; 195/80 R
[58] Field of Search ..................... 424/117; 195/80, 96

[56] References Cited
U.S. PATENT DOCUMENTS
4,031,206  6/1977  Celmer et al. ....................... 424/117

*Primary Examiner*—Jerome D. Goldberg
*Attorney, Agent, or Firm*—James W. Ambrosius

[57] ABSTRACT

A new antibiotic prepared from aerobic cultivation of *Actinoplanes sarveparensis* and a method for producing the same from a culture medium.

3 Claims, 2 Drawing Figures

ANTIBIOTIC SUBSTANCE FROM *ACTINOPLANES SARVEPARENSIS* CBS 305.76 (ANTIBIOTIC L 13365)

SUMMARY OF THE INVENTION

The present invention refers to a new antibiotic substance obtained by the fermentation of a strain belonging to the genus Actinoplanes, specifically *Actinoplanes sarveparensis*. The novel antibiotic substance, hereinafter referred to as antibiotic L 13365 is a light yellow crystalline compound having characteristic identifiable properties such as melting point, infrared and ultraviolet absorption maxima.

As stated above, antibiotic L 13365 is produced by cultivation of a fermenting strain named *Actinoplanes sarveparensis*. This strain, identified with out collection number A/13826, was isolated from a soil sample collected at Sarvepar Village, India. The strain has been deposited and made part of the stock culture collection of CBS (Centraal Bureau Voor Schimmelcultures — Oosterstraat 1 — Baarn — The Netherlands) where it was assigned the number 305.76.

In the preparation of antibiotic L 13365, the microorganism is cultivated under aerobic conditions in an aqueous nutrient medium containing an assimilable source of carbon, an assimilable source of nitrogen and inorganic salts.

As used herein, the term "assimilable source" refers to a source of a substance required for the growth of the organism or for the production of the antibiotic supplied in a form which may be absorbed and used by the organism.

Ordinarily, the antibiotic producing strain is precultured in a shake flask until substantial antibiotic activity is present then the culture is used to inoculate jar fermentors containing a nutrient fermentative medium.

The culture is normally incubated at from about 25°–35° C under aerobic conditions for a time sufficient to produce a substantial antibiotic level. During this time, microbiological assays are carried out by the agar diffusion method to control the concentration of the antibiotic substance produced.

After eliminating the mycelium cake by filtration, the antibiotic substance is recovered from the filtered fermentation broth by conventional procedures known to the art, such as, for instance, by extraction with an organic solvent in which the antibiotic substance is soluble and which is immiscible with the aqueous medium. The extraction is carried out after adjustment of the pH of the filtrate between about 2 to about 4. Suitable organic solvents for the extraction are advantageously selected from alkanols containing from 1 to about 6 carbon atoms, $(C_1-C_4)$alkyl esters of lower aliphatic acids, or lower halogenated hydrocarbons. The solvent may then be separated from the fermentation broth by high-speed centrifugation, concentrated to about 1/200–1/400 of its original volume, cooled and allowed to stand until a precipitate forms which may be recovered by filtration. This precipitate consists of antibiotic L 13365 substantially free of major impurities. The mother liquors are collected and poured into an excess of an inert non-polar solvent such as light petroleum or the like giving a further amount of crude antibiotic L 13365. The crude product thus obtained is dissolved in a methanol-acetone mixture and is precipitated from the solution by addition of acidic water.

The two portions are gathered together and may be further purified by column chromatography using a chloroform-methanol mixture as the eluting system.

Antibiotic L 13365 is finally crystallized from methanol:ethyl acetate having a 1:1 ratio.

DETAILED DESCRIPTION OF THE INVENTION

Figure 1:
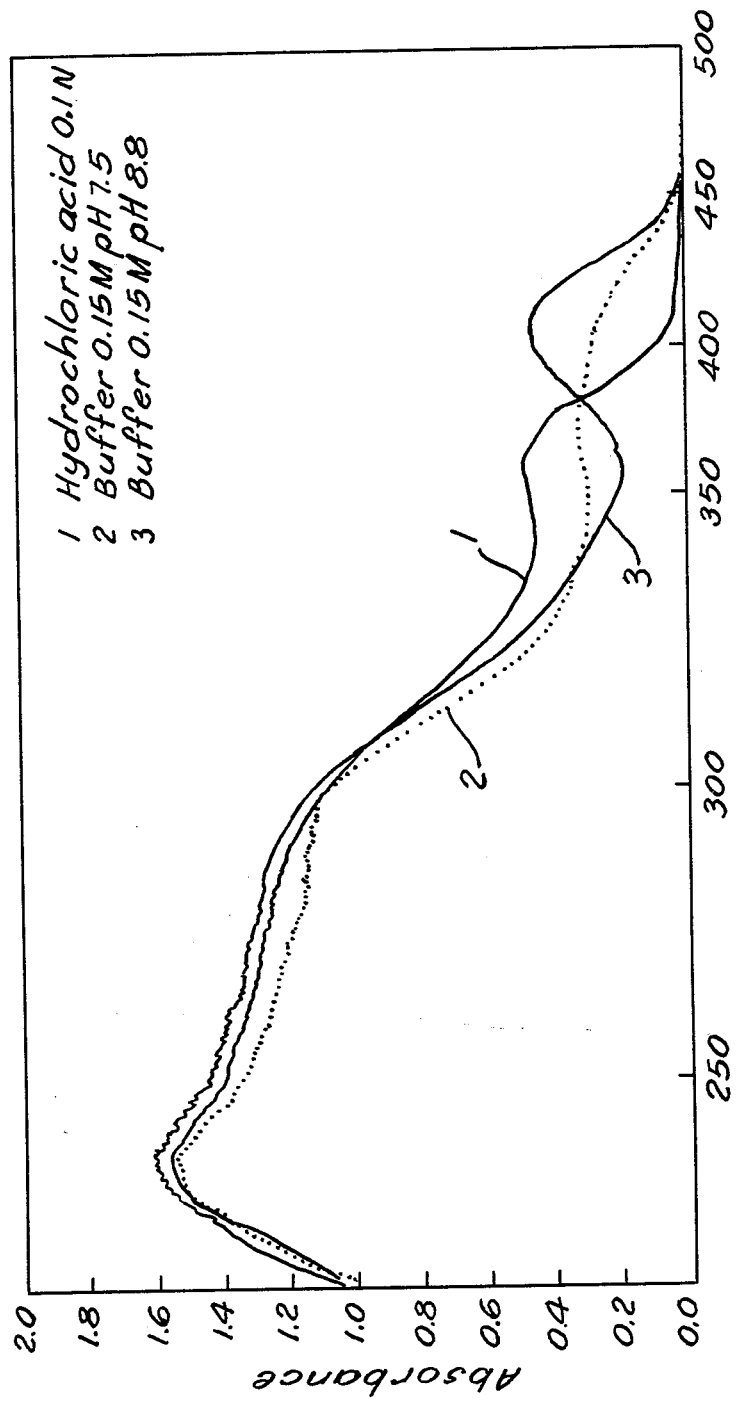
FIG. 1 is a typical ultraviolet spectrum of antibiotic L 13365 as recorded from a solution of methyl cellosolve.

The antibiotic substance L 13365 shows a remarkable antibacterial in vitro and in vivo activity. More particularly, antibiotic L 13365 exhibits an outstanding *in vitro* antimicrobial action, especially against gram-positive bacteria, as shown in Table I below.

TABLE I

| Strain | Minimal Inhibitory Concentration (μg/ml) |
|---|---|
| Staphylococcus aureus ATCC 6538 | 0.025 |
| Staphylococcus aureus Tour | 0.025 |
| Streptococcus haemolyticus C 203 | 0.0062 |
| Diplococcus pneumoniae UC 41 | 0.00078 |
| Clostridium perfringens ISS 30543 | 0.012 |
| Mycoplasma gallisepticum H21 CZB | 0.2 |

Furthermore, as stated above, antibiotic L 13365 also displays an excellent in vivo activity against experimental infections in mice. More particularly, the dose effective to protect 50 percent of the mice ($ED_{50}$) using antibiotic L 13365 against experimental infections provoked by *Staphylococcus aureus*, *Streptococcus haemolyticus* and *Diplococcus pneumoniae* are listed hereinbelow in Table II.

TABLE II

| Infection Strain | $ED_{50}$ mg/kg* s.c. |
|---|---|
| Streptococcus haemolyticus | 0.2 |
| Staphylococcus aureus | 10 |
| Diplococcus pneumoniae | 0.4 |

*median effective dose ($ED_{50}$)

The new antibiotic substance is active also against microorganism strains which are resistant to other commonly used antibiotics. Representative examples of the minimum inhibiting concentrations (MIC) of antibiotic L 13365 against *Staphylococcus aureus* strains resistant to several antibiotics are reported in Table III.

TABLE III

| Strain | MIC of Other Antibiotics | MIC of Antibiotic L 13365 |
|---|---|---|
| Staphylococcus aureus ATCC 6538 resistant to penicillin | penicillin >100 | 0.4 |
| Staphylococcus aureus Tour resistant to streptomycin | streptomycin >100 | 0.078 |
| Staphylococcus aureus ATCC 6538 resistant to tetracycline | tetracycline >100 | 0.15 |
| Staphylococcus aureus ATCC 6538 resistant to | rifampicin >100 | 0.01 |

TABLE III-continued

| Strain | MIC of Other Antibiotics | MIC of Antibiotic L 13365 |
| --- | --- | --- |
| refampicin | | |
| Staphylococcus aureus ATCC 6538 resistant to neomycin | neomycin >100 | 0.005 |
| Staphylococcus aureus ATCC 6538 resistant to erythromycin | erythromycin >100 | 0.04 |
| Staphylococcus aureus ATCC 6538 resistant to chloramphenicol | chloramphenicol >100 | 0.02 |
| Staphylococcus aureus ATCC 6538 resistant to cephaloridine | cephaloridine >100 | 0.078 |
| Staphylococcus aureus ATCC 6538 resistant to kanamycin | kanamycin >100 | 0.04 |
| Staphylococcus aureus ATCC 6538 resistant to bacitracin | bacitracin >100 | 0.02 |
| Staphylococcus aureus ATCC 6538 resistant to lincomycin | lincomycin >100 | 0.15 |

The toxicity of antibiotic L 13365, administered either orally or intraperitoneally to mice is very low with the median lethal dose ($LD_{50}$) values higher than 1000 mg/kg.

Description of *Actinoplanes sarveparensis* A/13826

Macroscopic examination of colonies

The strain grows well on various nutrient agars. In oatmeal agar, the colonies are 3 to 4 mm in diameter, show irregular contours and a rough surface. Aerial mycelium is always absent.

Microscopic examination

Sporangia are produced in several agar media. They have a regular globose shape with a diameter ranging from 13 to 20 μ. The zoospores, highly motile, are spherical but occasionally are slightly elongated with a diameter of 1.5–2 μ. On the basis of these characteristics, the strain A/13826 is ascribed to the genus Actinoplanes and given the name *Actinoplanes sarveparensis* CBS 305.76. Table IV reports the cultural characteristics of *Actinoplanes sarveparensis* CBS 305.76 cultivated on various standard media suggested by Shirling and Gottlieb (Intern. J. Syst. Bact., 16, 313–340, 1966) and other media recommended by Waksman (The Actinomycetes, Vol. II, The Williams and Wilkins Co., 1961). The cultural characteristics were determined after 6–14 days of incubation at 30° C.

Table V reports the utilization of carbon sources examined according to the method of Pridham and Gottlieb (Intern. J. Syst. Bact. 56, 107, 1948).

Table VI reports the physiological characteristics of the strain.

TABLE IV
Cultural Characteristics of *Actinoplanes sarveparensis* CBS 305.76

| Culture Medium | Cultural Characteristics |
| --- | --- |
| Medium No. 2 (yeast extract-malt agar) | Abundant growth, wrinkled surface, orange to brown; (central part of colony is darker). |
| Medium No. 3 (oatmeal agar) | Scant growth, thin, hyaline to light orange - production of sporangia. |
| Medium No. 4 (inorganic salts-starch agar) | Moderate growth, crusty surface, light orange (9/G/7). |
| Medium No. 5 (glycerol-asparagine agar) | Abundant growth, crusty surface, brilliant orange (9/I/11). |
| Medium No. 6 (peptone-yeast extract-iron agar) | Scant growth, crusty suface, brown (13/C/7). |
| Medium No. 7 (tyrosine agar) | Moderate growth, crusty surface, orange (11/F/8). |
| Oatmeal agar (according to Waksman) | Abundant growth, rough surface, orange (9/H/12), (central part of colony is darker). |
| Hyckey and Tresner's agar | Moderate growth, wrinkled surface brown (18/A/12). |
| Czapek glucose agar | Abundant growth, wrinkled surface orange (11/G/11). |
| Glucose asparagine agar | Abundant growth, rough surface, brilliant orange (9/I/11). |
| Nutrient agar | Moderate growth, rough surface, orange (11/F/8). |
| Potato agar | Moderate growth, wrinkled surface, orange to brown - production of sporangia. |
| Bennett's agar | Moderate growth, wrinkled surface, light orange (9/D/5). |
| Calcium malate agar | Scant growth, thin hyaline to light orange - production of sporangia. |
| Skim milk agar | Abundant growth, wrinkled surface, orange to light brown, patch shadows. |
| Czapek agar | Abundant growth, wrinkled surface, orange (11/G/11). |
| Egg agar | Scant growth, rough surface, hyaline. |
| Pept. glucose agar | Moderate growth, wrinkled surface, deep orange (11/B/12). |
| Agar | Very scant growth, thin, hyaline |
| Loeffler Serum | Very scant growth, orange |
| Potato | Scant growth, wrinkled, deep orange |
| Gelatin | Scant growth, light orange |
| Cellulose | No growth |

Color determination was made by the method of Maerz and Paul (Maerz, A. and M. Reg. Paul 1950. A dictionary of color, 2nd ed. M. Grow — Hill Book Company, Inc., New York).

The numbers of some culture media refer to those given according to Shirling and Gottlieb (Intern. J. Syst. Bact., 16, 313–340, 1966).

TABLE V

| Utilization of Carbon Compounds | |
| --- | --- |
| Carbon Sources | Utilization |
| $C_5$ Arabinose | + |
| Xylose | + |
| $C_6$ Glucose | + |
| Fructose | + |
| Mannose | + |
| Mannitol | + |
| Inositol | + |
| Rhamnose | + |
| $(C_6)_2$ Sucrose | + |
| Lactose | + |

TABLE V-continued

| Utilization of Carbon Compounds | |
|---|---|
| Carbon Sources | Utilization |
| (C₅)₃ Raffinose | − |
| (C₆)₄ Cellulose | − |
| Special Salicin | − |

+ means utilization
− means lack of utilization

TABLE VI

| Physiological Characteristics | |
|---|---|
| Test | Results |
| Hydrolysis of starch | positive |
| H₂S formation | positive |
| Melanin production | negative |
| Tyrosinase reaction | negative |
| Casein hydrolysis | positive |
| Calcium malate hydrolysis | positive |
| Nitrate reduction | positive |
| Litmus milk coagulation | negative |
| Litmus milk peptonization | positive |
| Gelatin liquefaction | positive |

Production and Isolation of the Antibiotic Substance

A preferred method for producing the antibiotic substance is by aerobically pre-culturing the *Actinoplanes sarveparensis* CBS 305.76 in a nutrient medium until substantial antibiotic activity is present at a pH value ranging from about 6 to about 10. The following shake flask culture was found satisfactory in the practice of the present invention.

| Meat extract | 3.0 g/l |
|---|---|
| Tryptone | 5.0 g/l |
| Yeast extract | 5.0 g/l |
| Glucose | 1.0 g/l |
| Soluble starch | 24.0 g/l |
| Calcium carbonate | 4.0 g/l |
| Distilled water | q.s. to 1000 ml |

The flakes are shaken for about 24 hours at about 28°–30° C and the pre-cultures (one liter) are used to inoculate jar fermentors each containing 10 liters of the following nutrient medium:

| Meat extract | 40 g |
|---|---|
| Peptone | 40 g |
| Yeast extract | 10 g |
| Sodium chloride | 25 g |
| Soybean meal | 100 g |
| Glucose | 500 g |
| Calcium carbonate | 50 g |
| Tap water | q.s. to 10 liters |

The fermentation batches are incubated aerobically under stirring at 28°–30° C. At intervals, the antibiotic activity is assayed microbiologically by the agar diffusion method using *Staphylococcus aureus* as the test organism. The maximum activity will be reached after about 72–96 hours of fermentation.

Isolation and Purification of Antibiotic L 13365

One method of isolating the enzyme found to be satisfactory was as follows: the fermentation broth (80 liters) was filtered using 1 percent clarcel (W/V) as a filter aid. The mycelium cake is discarded and the filtered solution, acidified to pH 2.5 with 10 percent HCl, is extracted twice with an amount of ethyl acetate corresponding to about 50 percent of its volume.

The organic phase was separated from the aqueous one by means of high-speed centrifugation, then dried over $Na_2SO_4$, concentrated at 45°–50° C under vacuum to about 1/300 of its orginal volume and finally cooled to about 0°–10° C.

A crude precipitate formed, which was collected on a filter, washed with a small quantity of ethyl acetate and dried at about 45° C under vacuum. 1.140 Grams of the antibiotic substance L 13365 were obtained with a purity degree of about 70 percent, determined spectrophotometrically.

The mother liquors deriving from the above filtration were poured into 20 volumes of light petroleum and an additional amount (2.550 g) of antibiotic substance with a purity degree of 20–25 percent (determined spectrotometrically) was obtained. This substance was suspended in a small amount of methanol:acetone 9:1 mixture, filtered from any insoluble impurities and diluted with water: the solution was brought to a pH value of about 2.5 by means of 10 percent HCl under stirring and the precipitate which formed was collected by centrifugation and redissolved in a minimum amount of butanol at about 45°–50° C. The solution was concentrated under vacuum to about 1/5 of the original volume and cooled to about 4° C. The resulting precipitate, after being collected and dried under vacuum, was the antibiotic substance L 13365 (0.450 g) having a purity degree of about 80 percent (determined spectrophotometrically). The obtained crops were then subjected to common purification operations known to the art. To this purpose, they were dissolved in a minimum amount of a chloroform:methanol 85:15 mixture and chromatographed through a silica-celite column (1:1 V/V), previously activated at 100° C, and washed with the above chloroform/methanol mixture.

Elution and thin layer chromatography control of the fractions are performed with the same mixture. The fractions collected according to t.l.c. analysis data were concentrated under vacuum to a small volume. Upon adding diethyl ether, a precipitate formed, consisting of antibiotic L 13365 with a purity degree of about 95 percent (determined spectrophotometrically). Said precipitate was dissolved in a methanol:ethyl acetate 1:1 mixture, heated to 45° C and filtered from any insolubles; upon cooling to 4° C and standing overnight at the same temperature substantially pure antibiotic L 13365 was obtained a light yellow needles.

Chemico-physical Properties of Antibiotic L 13365

Antibiotic L 13365 is a light yellow crystalline powder with acidic character. Analysis of an acid hydrolisate of antibiotic L 13365 in 6N hydrochloric acid in a sealed tube at 110° C revealed four amino acids, three of them have been identified in an amino acid autoanalyzer as aspartic acid, threonine and glycine. Furthermore, antibiotic L 13365 is characterized by the following properties:

(1) Melting point: — 210° C
(2) Elemental analysis: — C = 51.35, H = 5.05, N = 10.50, S = 11.05 and O (by difference) = 22.05.
(3) Ultraviolet and visible absorption spectrum

| Solvent | $\lambda_{max}$ (nm) | $E^{1\%}_{1cm}$ |
|---|---|---|
| Hydrochloric acid 0.1N | 360 | 103 |
| | 290 (shoulder) | |
| | 237 | 326 |
| Buffer 0.15 M pH 7.5 | 408 (shoulder) | |
| | 378 | 67 |
| | 290 (shoulder) | |
| | 237 | 326 |
| Buffer 0.15 M pH 8.8 | 408 | 99 |
| | 290 (shoulder) | |

-continued

| Solvent | $\lambda_{max}$ (nm) | $E^{1\%}_{1cm}$ |
|---------|---------------------|-----------------|
|         | 238                 | 336             |

Ultraviolet absorption spectra were determined with a UNICAM Sp 800 ultraviolet spectrophotometer using solutions of L 13365 in methylcellosolve (MCS)-buffers at different pH in one to one proportion. The complete ultraviolet spectrum is shown in FIG. 1.

(4) Fluorescence spectrum: — The antibiotic contains a strongly fluorescent chromophore and a solution of the product in 0.1 N sodium hydroxide excited at 240 nm shows an emission spectrum with maxima at 355 and 490 nm. Fluorescense spectrum was determined with a Perkin Elmer Mod. MPF — 44 fluorescence spectrophotometer.

Figure 2:
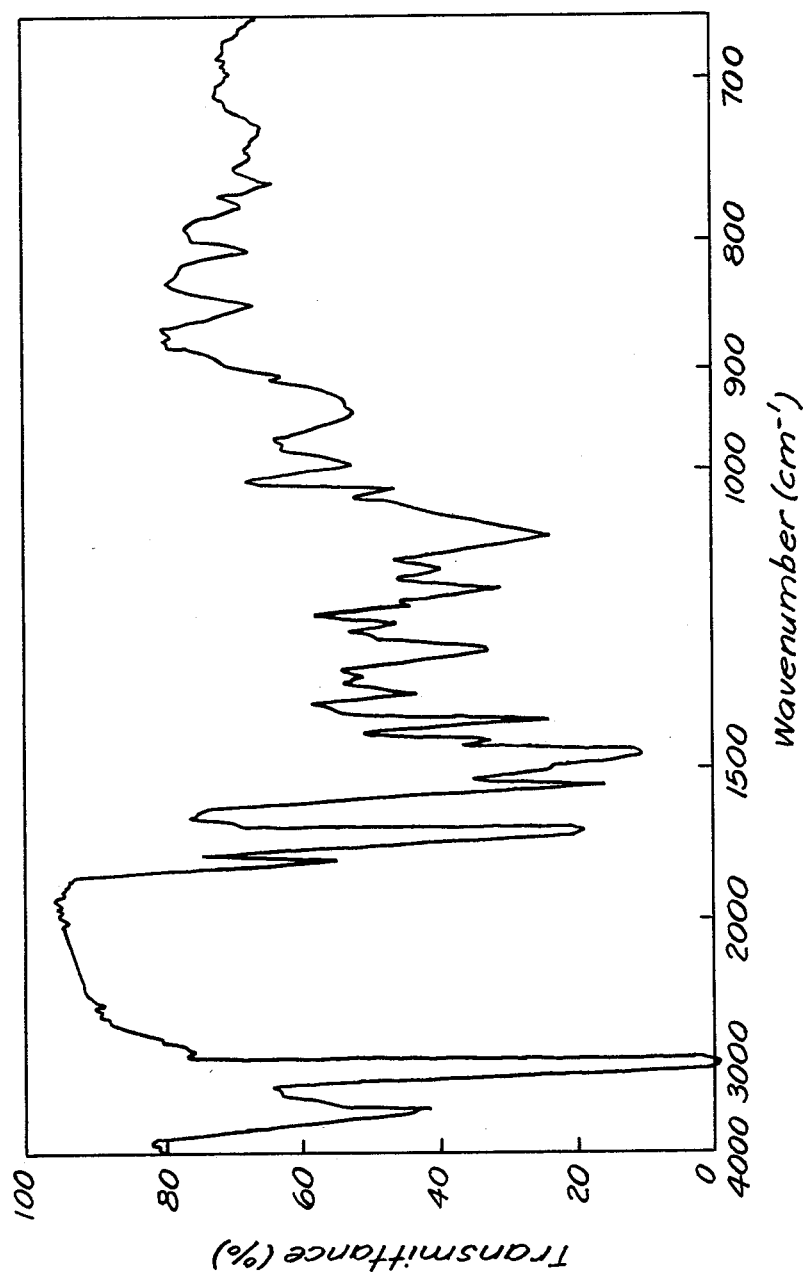
FIG. 2 represents a typical infrared spectrum of antibiotic L 13365.

(59 Infrared spectrum: — Characteristic absorption bands in nujol have been observed at the following frequencies (cm$^{-1}$): 3400 (shoulder), 3350 (sharp), 3200 (shoulder), 3100 (sharp), 2930 and 2870 (nujol), 2800–2400, 2380 (atmospheric carbon dioxide), 1750 (sharp), 1670 (sharp), 1620 (sharp), 1540 (sharp), 1480 (sharp), 1460 and 1380 (nujol), 1420 (sharp), 1340 (sharp), 1320 (sharp), 1280 (sharp), 1240 (sharp), 1195 (sharp), 1170 (sharp), 1145 (sharp), 1120 (sharp), 1075 (broad), 1015 (sharp), 990 (sharp), 935 (sharp), 920 (broad), 900 (sharp), 865 (sharp), 840 (sharp), 800 (sharp), 770 (sharp), 755 (sharp), 740 (sharp), 720 (nujol). The infrared spectrum was determined with a Perkin Elmer Mod. 157 spectrophotometer. The complete infrared spectrum is shown in FIG. 2.

(6) Specific rotation: — $[\alpha]_{436}^{25}$ = + 125° (C = 0.8 percent in methanol:chloroform 1:1)

(7) Solubility: — The compound is soluble in dimethylsulfoxide, dimethylformamide and in chloroform/methanol mixtures; slightly soluble in chloroform, methanol, methanol/ethyl acetate mixtures, sodium bicarbonate solutions and glacial acetic acid; insoluble in water and in the other common organic solvents.

(8) Characteristic reactions

| Fehling | positive |
| Tollens | positive |
| KMnO$_4$ | positive |
| H$_2$SO$_4$ conc. | dark brown color |
| Ninhydrin | negative |
| FeCl$_3$ | positive |
| Millon | negative |
| Schiff | negative |
| Anthrone | positive |
| Folin Ciocalteau | negative |
| Elson Morgan | negative |

(9) Acidity: An ionizable function with pK$_a$ 7.8 is evidenced by potentiometric titration with 0.1 N sodium hydroxide of antibiotic L 13365 in a 2-methoxyethanol:water 4:1 solution. The equivalent weight determined accordingly is 1400.

(10) Chromatographic behavior

| Solvent System | Rf* |
|----------------|-----|
| Buffer pH 6.0 saturated n-butanol | 0.75 |
| Water saturated n-butanol + 2% p-toluenesulfonic acid | 0.80 |
| Water saturated n-butanol + 2% conc. ammonia | 0.70 |
| Butanol saturated buffer pH 6.0 | 0.0 |
| Ammonium chloride (20% W/V in water) | 0.0 |
| n-butaniol:methanol:water 40:10:20 containing 0.75 g methyl orange | 0.90 |
| n-butaol:methanol:water 40:10:30 | 0.90 |
| water:acetone 1:1 | 0.35 |
| water saturated ethyl acetate | 0.0–0.31 |
| chloroform:methanol 85:15 (**) | 0.51 |

(*) = Paper chromatography on Whatman paper no. 1. Antibiotic visualized on agar plates seeded with *S. aureus*.
(**) = Tlc on silica gel plates HF/UV$_{254}$. Fluorescent spot under ultraviolet light.

What is claimed is:

1. Antibiotic L 13365, said antibiotic having the following characteristics:

(a) Melting point: 210° C;
(b) Approximate elemental composition of 51.35 percent carbon, 5.05 percent hydrogen, 10.50 percent nitrogen, 11.05 percent sulfur and 22.05 percent oxygen;
(c) Ultraviolet spectrum: characteristic ultraviolet absorption bands in the following solvent systems

| Solvent | $\lambda_{max}$ (nm) | $E^{1\%}_{1cm}$ |
|---------|---------------------|-----------------|
| Hydrochloric acid 0.1N | 360 | 103 |
|  | 290 (shoulder) |  |
|  | 237 | 326 |
| Buffer 0.15 M pH 7.5 | 408 (shoulder) |  |
|  | 378 | 67 |
|  | 290 (shoulder) |  |
|  | 237 | 326 |
| Buffer 0.15 M pH 8.8 | 408 | 99 |
|  | 290 (shoulder) |  |
|  | 238 | 336 |

(d) Infrared spectrum: characteristic infrared absorption bands in nujol at the following frequencies (cm$^{-1}$): 3400 (shoulder), 3350, 3200 (shoulder), 3100 (sharp), 2930 and 2870 (nujol), 2800–2400, 2380 (atmospheric carbon dioxide), 1750 (sharp), 1670 (sharp), 1620 (sharp), 1540 (sharp), 1480 (sharp), 1460 and 1380 (nujol), 1420 (sharp), 1340 (sharp), 1320 (sharp), 1280 (sharp), 1240 (sharp), 1195 (sharp), 1170 (sharp), 1145 (sharp), 1120 (sharp), 1075 (broad), 1015 (sharp), 990 (sharp), 935 (sharp), 920 (broad), 900 (sharp), 865 (sharp), 840 (sharp), 800 (sharp), 770 (sharp), 755 (sharp), 740 (sharp), 720 (nujol);

(e) Specific rotation: — $\alpha]_{436}^{25}$ = +125° (C = 0.8 percent in methanol:chloroform 1:1);

(f) Solubility: — Soluble in dimethylsulfoxide, dimethylformamide and in chloroform/methanol mixtures. Slightly soluble in chloroform, methanol, methanol/ethyl acetate mixtures, sodium bicarbonate solutions and glacial acetic acid; insoluble in water and in the other common organic solvents;

(g) Characteristic reactions:

| Fehling | positive |
| Tollens | positive |
| KMnO$_4$ | positive |
| H$_2$SO$_4$ conc. | dark brown color |
| Ninhydrin | negative |
| FeCl$_3$ | positive |
| Millon | negative |
| Schiff | negative |
| Anthrone | positive |
| Folin Ciocalteau | negative |
| Elson Morgan | negative |

(h) Ionizable functions: an ionizable function potentiometrically evidenced with $pK_a$ = 7.8 (2-methoxyethanol:water 4:1);

(i) R.F. values: chromatography on Whatman paper No. 1; Visualization of the spots by microbiological development on *Staphylococcus aureus*

| Eluting System | Rf value |
|---|---|
| Buffer pH 6.0 saturated n-butanol | 0.75 |
| Water saturated n-butanol + 2% p-toluenesulfonic acid | 0.80 |
| Water saturated n-butanol + 2% conc. ammonia | 0.70 |
| Butanol saturated buffer pH 6.0 | 0.0 |
| Ammonium chloride (20% W/V in water) | 0.0 |
| n-butanol:methanol:water 40:10:20 containing 0.75 g methyl orange | 0.90 |
| n-butanol-methanol:water 40:10:30 | 0.90 |
| water:acetone 1:1 | 0.35 |
| water saturated ethyl acetate | 0.0–0.31 |
| chloroform:methanol 85:15 | 0.51 |

2. The method of producing antibiotic L 13365 as defined in claim 1 which comprises cultivating *Actinoplanes sarveparensis* CBS No. 305.76 in a culture medium containing an assimilable source of carbon, an assimilable source of nitrogen and inorganic salts under submerged aerobic conditions until a substantial amount of antibiotic L 13365 is produced by said organism in said culture medium.

3. The method of claim 2 which includes the additional step of isolating antibiotic L 13365 as defined in claim 2 from said culture medium.

* * * * *

UNITED STATES PATENT AND TRADEMARK OFFICE
CERTIFICATE OF CORRECTION

PATENT NO. : 4,100,273

DATED : July 11, 1978

INVENTOR(S) : Hermes Pagani, et al

It is certified that error appears in the above-identified patent and that said Letters Patent are hereby corrected as shown below:

Column 1, line 17, "out" should read -- our --.

Column 2, line 35, "perfringens" should read --perfingens--.

Column 2, line 49, "pnemoniae" should read --pneumoniae--.

Column 5, line 67, "centrifugation" should read --configuration--.

Column 6, line 1, "orginal" should read --original--.

Column 6, line 13, "trotometrically)" should read --trophotometrically)--.

Column 6, line 45, "obtained a light" should read --obtained as light--.

Column 7, line 16, "MPF" should read --MPP--.

Column 7, line 18, "(59 Infrared" should read --(5) Infrared--.

Column 7, line 67, "n-butaniol:" should read --n-butanol:--.

Column 7, line 69, "n-butaol:" should read --n-butanol:--.

UNITED STATES PATENT AND TRADEMARK OFFICE
CERTIFICATE OF CORRECTION

PATENT NO. : 4,100,273

DATED : July 11, 1978

INVENTOR(S) : Hermes Pagani, et al

It is certified that error appears in the above-identified patent and that said Letters Patent are hereby corrected as shown below:

Column 8, line 9, "()=Tic" should read --()=Tlc--.

Column 9, line 17, insert --Thin layer chromatography on silica gel plates $HF/UV_{254}$. Visualization of the fluorescent spot under the ultra-violet light.--.

Column 10, line 16, "claim 2" should read --claim 1--.

Signed and Sealed this

Sixth Day of February 1979

[SEAL]

Attest:

RUTH C. MASON
*Attesting Officer*

DONALD W. BANNER
*Commissioner of Patents and Trademarks*